Figure 1:
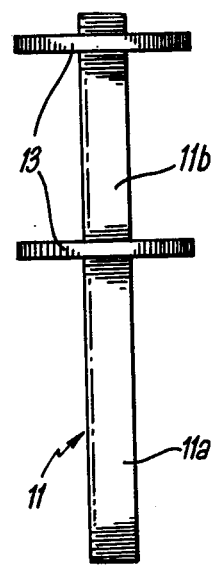

United States Patent [19]

Kurer

[11] 4,203,217
[45] May 20, 1980

[54] ATTACHMENT OF TOOTH CROWNS
[75] Inventor: Peter F. Kurer, Cheadle, England
[73] Assignee: Pinnockchoice Limited, Manchester, England
[21] Appl. No.: 938,021
[22] Filed: Aug. 30, 1978
[30] Foreign Application Priority Data
Sep. 9, 1977 [GB] United Kingdom ............... 37690/77
[51] Int. Cl.² ............................................. A61C 5/08
[52] U.S. Cl. .................................................. 433/220
[58] Field of Search ..................................... 32/13, 12
[56] References Cited
U.S. PATENT DOCUMENTS
1,248,242 11/1917 Babcock .................................. 32/12
FOREIGN PATENT DOCUMENTS
931255 9/1956 Fed. Rep. of Germany .............. 32/13

Primary Examiner—Robert Peshock
Attorney, Agent, or Firm—Sughrue, Rothwell, Mion, Zinn and Macpeak

[57] ABSTRACT

A post for attaching a tooth crown to a natural tooth root is disclosed which comprises a screw-threaded shank having a plurality of collars in screw-threaded engagement therewith, the collars being adjustable axially of the shank. A method of attaching a tooth crown using the post as aforesaid is also disclosed, the method including the steps of engaging the shank with a pre-prepared tooth root, locating the collars in a requisite relative disposition on the shank, preferably with a collar against the tooth root face providing a shaped head on the shank and within which the collars are at least partially embedded, and applying a crown to the said shaped head.

3 Claims, 2 Drawing Figures

U.S. Patent

May 20, 1980

4,203,217

ATTACHMENT OF TOOTH CROWNS

The invention concerns the attachment of tooth crowns.

Means for attaching a tooth crown to a tooth root are known which comprise a threaded stainless steel rod of sufficiently small diameter to be screwed into a pre-prepared tooth root canal, there being a head at one end of the rod of dimensions appropriate to the context.

The head of the attachment means aforesaid is initially of constant transverse cross-section and, in use, the underside thereof is seated on the tooth root face, and head being ground to shape in situ to receive a tooth crown having a cavity therein complementary to the ground shape of the head.

Whilst the attachment means as aforesaid has been widely adopted, there are limitations or disadvantages, the principal ones of which relate to the cross-sectional form of the head in relation to the corresponding cross-section of a tooth and to the range of tooth heights involved in practising the method to which the attachment means relate.

The primary object of the present invention is to provide an improved form of attachment means.

According to the invention there is proposed an attachment means for engagement with a tooth root and adapted to receive a tooth crown which comprises a shank for engagement with a pre-prepared tooth root canal and at least one collar provided on such shank and adjustable axially thereof, the shank being of a non-corrodible material appropriate to the context of dentistry.

According to a preferred feature the shank is a screw-threaded shank and the or each axially adjustable collar is screw-threadedly engaged with such shank.

According to a further preferred feature, a plurality of collars is provided and the axially extreme collars are adjustable axially of the shank.

Figure 2:
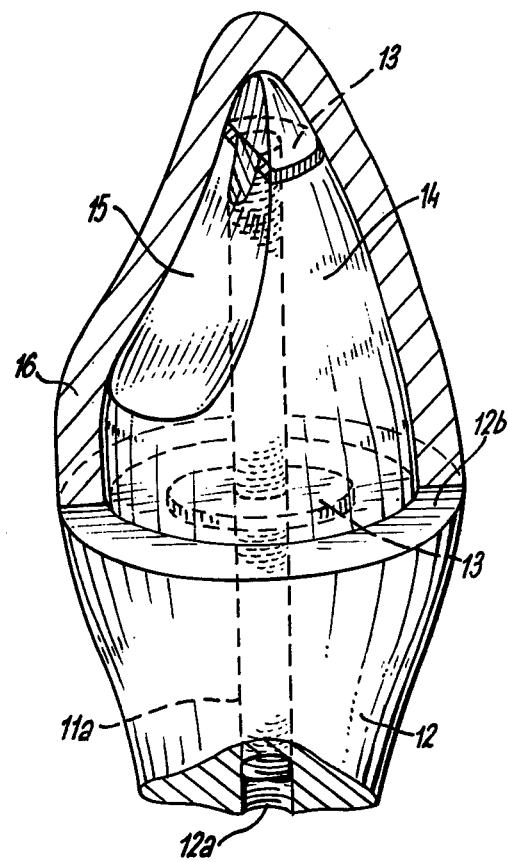

The invention will now be described further, by way of example only, with reference to the accompanying drawing which illustrates one embodiment thereof and in which:

FIG. 1 is a side elevation of an attachment means constructed in accordance with the invention; and FIG. 2 is a diagrammatic perspective view of the means as shown in FIG. 1 in use.

Referring now to the drawings, an attachment means for use in the attachment of a tooth crown to a tooth root comprises a threaded shank 11 of which the lower end 11a is for engagement with a complementarily screw-threaded blind hole 12a in the root canal of the said tooth root 12 and of which the upper end 11b carries two collars or fins 13 in screw-threaded engagement therewith, the said collars or fins being positionally adjustable axially of the shank 11 by selective rotation thereon.

The threaded shank 11, or post, is of a length and cross-sectional dimension of like order of magnitude to that post disclosed in prior British Patent specification No. 1,092,982 and is similarly of a precious metal, stainless steel or other material conventionally used in the dental art. The collars or fins are of a diameter, or equivalent, of like order of magnitude to the diameter, or equivalent, of the head of the post of the prior British Specification aforesaid.

In contradistinction to the prior art arrangement, the shank 11 of the present invention does not have a head formed integrally therewith or secured thereto prior to application of the threaded rod to the drilled and tapped tooth root, but rather a head or "core" 14 is built up on the upper end 11b of the shank when such shank is in position relative to the tooth root, the head or core 14 being formed from, for example, a dental composite as conventionally used for filling purposes and being applied to the shank and to the collars. Other materials from which the core might be formed include those self-polymerising plastics as currently used in dentistry, or a glassionomer cement likewise known in the art.

The head or core 14 may be "shaped" to a requisite form by application thereto of a preformed cover, not shown, whilst the material of the core is still soft, the cover being removed or otherwise, as preferred, on setting of the core.

In the event that the core is not shaped as by the use of a preformed cover, then a requisite shape, as at 15, is attained by suitably grinding the core when the material thereof has set. Whilst it is preferred that the grinding step does not involve the grinding of the material of the collars or fins 13, in some circumstances grinding of such elements is necessary in order to achieve a requisite shape.

The location of the collars or fins axially of the shank will be a matter of choice, but ordinarily the lowermost collar will abut the tooth root face 12b and the uppermost such collar will be adjacent the remote end of the shank.

The collars, although shown circular, will preferably be of non-circular form, thereby to introduce an anti-rotation characteristic as between the collars and the head or core, and such characteristic will be enhanced still further by providing a serrated periphery and/or surface to the collars. It may be found advantageous for the non-circular collars to be of a shape to correspond to the basic transverse cross-section of the tooth to be crowned.

The attachment means as herein proposed and the manner of use thereof offers a variety of advantages over the prior art arrangement and its manner of use. Thus, for example, the attainment of a requisite shape for the head is much facilitated in that the amount of metal to be removed is reduced, if indeed the need to remove metal is not wholly eliminated, whilst the use of a preformed cover either for shaping the head (if removed on setting of the material of the head) or for providing a shaped outer skin to the head (if retained in position on setting of the material of the head) will allow of the use of a crown 16 of constant wall thickness, thereby to avoid localised regions of high stress in such crown.

Furthermore, the facility for adjustment of the collars axially of the shank will much facilitate the adjustment of the length of such shank to accord to the depth of the pre-prepared hole in the tooth root canal.

An important advantage lies in the locking effect which arises from the tightening of the lower fin or collar against the tooth root face, such collar serving as a "locknut" and securing the post against subsequent rotation in the tooth root.

The invention is not restricted to the exact features of the embodiment disclosed, since alternatives will readily present themselves to one skilled in the art.

Thus, for example, whilst in the embodiment both of the collars or fins are screw-threadedly engaged with the shank, it may be found convenient for one of the collars to be fixed, especially if more than two collars are provided.

In some circumstances, particularly when intended for use with a lower tooth of small vertical dimension it may be sufficient for a single collar or fin to be used, in which case such collar or fin will be adjustable axially of the shank.

Furthermore, whilst the provision of a threaded shank for screw-threaded engagement with a tooth root and screw-threadedly to receive the or each axially adjustable collar is proposed, we may prefer in some instances, to use a shank of which that part intended for engagement with the tooth root is not screw-threaded, and to rely upon some alternative means for maintaining engagement of the shank with the root.

What is claimed is:

1. A method of attaching a tooth crown to a natural tooth root having a prethreaded root canal comprising the steps of:

engaging a threaded post with the previously prepared prethreaded tooth root canal, locating a plurality of collars screw threadedly engaged with the post axially on the post and in requisite spaced disposition thereon, tightening one of the collars against the tooth root face, positioning the other collar outwardly of the tooth root face in spaced relationship with such collar tightened against the tooth root face, creating an in situ shaped head on the post and the collars, and securing a crown to the shaped head.

2. The method as claimed in claim 1, wherein the head is shaped in situ by grinding a formed body.

3. The method as claimed in claim 1, wherein the head is shaped by utilising a pre-formed cover applied during the creation of the shaped head from a dental composite and before the hardening thereof.

* * * * *